United States Patent [19]

White

[11] Patent Number: 5,139,518

[45] Date of Patent: Aug. 18, 1992

[54] METHODS EMPLOYED IN REPLACEMENT OF THE CORNEAL ENDOTHELIUM

[76] Inventor: Thomas C. White, 1701 S. Minnesota Ave., Sioux Falls, S. Dak. 57105-1765

[21] Appl. No.: 496,633

[22] Filed: Mar. 21, 1990

Related U.S. Application Data

[63] Continuation-in-part of PCT/US88/03207, Sep. 19, 1988, continuation-in-part of Ser. No. 460,839, Jan. 23, 1990, Pat. No. 5,030,230, which is a continuation-in-part of Ser. No. 130,748, Dec. 9, 1987, Pat. No. 4,772,283, which is a continuation-in-part of Ser. No. 864,002, May 16, 1986, abandoned.

[51] Int. Cl.$^5$ .............................................. A61F 2/14
[52] U.S. Cl. ......................................... 623/5; 606/166
[58] Field of Search ...................... 623/4, 5; 606/166; 128/898

[56] References Cited

U.S. PATENT DOCUMENTS

| | | | |
|---|---|---|---|
| 2,714,721 | 8/1955 | Stone, Jr. ................................ | 623/5 |
| 3,458,870 | 8/1969 | Stone, Jr. ................................ | 623/6 |
| 4,077,411 | 3/1978 | Ward ....................................... | 606/166 |
| 4,236,519 | 12/1980 | La Russa et al. ....................... | 606/166 |
| 4,563,779 | 1/1986 | Kelman .................................... | 623/5 |
| 4,842,599 | 6/1989 | Bronstein ................................ | 623/5 |

OTHER PUBLICATIONS

Morgan, K., et al; "Five Year Follow-up of Epikeratophakia in Children," 93 Ophthal. 423-432 (1986).

Primary Examiner—Randy C. Shay
Attorney, Agent, or Firm—Fredrikson & Byron

[57] ABSTRACT

Prosthetic devices and methods are described that can be employed in replacing corneal endothelial tissue to allow the diseased or damaged corneal endothelial tissue to be replaced without replacing the outer layers of the patient's cornea and/or to replace the full thickness of the cornea in a manner resulting in less deformation of the outermost surface of the cornea (i.e. less astigmatism) than occurs with current full thickness transplant techniques. A partial outer thickness of tissue is removed from a patient's cornea by making a cut generally transverse to the axis of vision; a plug of the remaining portion of the patient's cornea from the area in which the outer thickness of tissue was removed is removed, the plug including Descemet's membrane and corneal endothelial cells, thereby forming a bore through the cornea; and an ocular implant sized and shaped to fit closely in said bore and to cover the area of the remaining portion of the patient's cornea from which the outer thickness of tissue was removed is placed in the bore. A corneal prosthesis of the invention includes a dome-shaped anterior cap component sized and configured to replace a partial thickness anterior portion of a cornea of an eye, and a posterior plug component extending posteriorly of the anterior portion sized and configured to replace a full thickness portion of the cornea, the plug component having a width smaller than the width of the cap component.

12 Claims, 3 Drawing Sheets

METHODS EMPLOYED IN REPLACEMENT OF THE CORNEAL ENDOTHELIUM

RELATED APPLICATIONS

This application is a continuation-in-part of co-pending International Application Ser. No. PCT/US88/03207, filed Sep. 19, 1988, and filed in the United States on Jan. 23, 1990 as Ser. No. 460,839, now U.S. Pat. No. 5,030,230 which is a continuation-in-part of U.S. patent application Ser. No. 130,748, filed Dec. 9, 1987, now U.S. Pat. No. 4,772,283, which in turn was a continuation-in-part of U.S. patent application Ser. No. 864,002, filed May 16, 1986, now abandoned.

FIELD OF THE INVENTION

This invention relates to prosthetic devices and methods for repairing and/or replacing damaged corneal tissue and particularly to such devices and methods as may be employed to replace damaged corneal endothelial tissue.

BACKGROUND OF THE INVENTION

For various reasons, the corneal portions of eyes must be surgically repaired or replaced. For example, the cornea may become scratched or scarred or otherwise physically damaged, greatly hindering sight. The cornea is also subject to the effects of various degenerative diseases, mandating replacement if the patient is to have normal or even near normal vision.

The cornea of the human eye is a specialized structure made up of substantially parallel relatively compacted layers of tissue. The outermost or most superficial layer of the cornea is the epithelial layer. This is a protective layer of tissue which regenerates if injured. Moving inwardly in the eye is the base surface of the epithelial layer known as Bowman's membrane. Immediately adjacent the Bowman's membrane is the stroma of the cornea, which is an extra-cellular collagen architectural matrix with scattered keratocytic cells. The stroma layer is bounded at its deepest level by a cuticular, a cellular membrane, referred to as Descemet's membrane, which is followed by a monolayer of single cell thickness of specialized endothelial cells which forms the posterior surface of the cornea. The endothelial layer does not regenerate and when it is diseased, scratched or otherwise injured, it must be replaced.

When disease or injury affect only the mid- or superficial stromal tissue and epithelial layer, as in certain scars, replacement of the superficial or a partial thickness of the anterior stroma may be sufficient to rehabilitate vision in the eye and a lamellar keroplasty or partial thickness transplant can be used. When, however, deep stroma and especially when the endothelium is diseased, those layers must be replaced and a full thickness or penetrating transplant is necessary.

A partial thickness transplant typically involves the replacement of a variable thickness of the outermost layers of the cornea but does not include replacement of the deep lining of Descemet's membrane and endothelial cell layer. The diseased tissue is replaced with an implant which may be a graft of tissue taken from the healthy cornea of a donor eye similar in size and shape to the tissue removed from the patient's cornea ("lamellar graft") or an artificial implant similar in size and shape to the tissue removed from the patient's cornea and made of a biologically acceptable material.

A full thickness transplant typically involves the replacement of all layers of the cornea, including the deep Descemet's membrane and the layer of endothelial cells. A cylindrical plug of the corneal tissue is replaced with a cylindrical implant which may be a plug of tissue cut from a donor cornea through the full thickness of corneal tissue ("penetrating graft") or an artificial implant sized and shaped to fit in a bore surgically formed through a patient's cornea.

The shape of the outermost surface of the cornea influences the quality of vision and changes made in the curvature of that surface can result in regular or irregular astigmatism or a change in the refractive state of the eye. Therefore, it would be desirable to be able to replace the deepest corneal layers without having to replace healthy tissue on the outermost surface of the cornea and to minimize deformation of the outermost corneal surface when all layers of corneal tissue must be replaced.

SUMMARY OF THE INVENTION

This invention relates to prosthetic devices and methods employed in replacing corneal endothelial tissue that allows the diseased or damaged corneal endothelial tissue to be replaced without replacing the outer layers of the patient's cornea and/or replacing the full thickness of the cornea in a manner resulting in less deformation of the outermost surface of the cornea (i.e. less astigmatism) than occurs with current full thickness transplant techniques.

A method of the invention comprises the steps of removing a partial, thickness of outer layers of corneal tissue from a patient's cornea using a generally transverse cut, removing a plug of the remaining portion of the patient's cornea from the area in which the outer thickness of tissue was removed, the plug including Descemet's membrane and corneal endothelial cells, thereby forming a bore through the remaining portion of the patient's cornea, and placing in the bore an ocular implant sized and shaped to fit closely in the bore and to fit into and to cover the area of the cornea from which the tissue was removed by the transverse cut so that the resulting shape of the outermost surface of the patient's cornea is substantially the same as its pre-transplant shape.

In a preferred embodiment, the ocular implant comprises a replacement plug sized and shaped to fit closely in the bore and a replacement cap sized and shaped to simulate the thickness of outer layers of tissue, the outer layers including the epithelial cell layer, Bowman's membrane and a variable amount of the corneal stroma and having been removed from the patient's cornea. In this embodiment, the method further comprises the steps of placing the replacement plug into the bore, attaching the plug to the cornea, placing the replacement cap into the area of the cornea from which the thickness of outer layers of tissue was removed and attaching the cap to the cornea. The replacement plug and replacement cap may each be made either of an artificial material or be obtained from the cornea of a healthy donor eye. When the outer layers of a patient's cornea are not diseased and only corneal endothelial tissue must be replaced, the method may include the step of reattaching the thickness of outer layers of the patient's cornea initially removed.

In another embodiment of the invention, the method comprises the steps of cutting through the full thickness of a patient's cornea to form a plug, the plug having a beveled edge and an inner and outer surface and wherein the beveled edge slopes toward the center of the cornea from the outer surface to the inner surface, removing the plug to form a bore through the corneal tissue remaining and placing in the bore an ocular implant sized and shaped to fit closely in the bore and so that the resulting shape of the outermost surface of the patient's cornea is substantially the same as its pre-transplant shape.

The invention also relates to an ocular prosthesis for replacing the full thickness of the cornea, the prosthesis having an replacement plug component, generally sized and configured to fit into a bore formed in a rim in a patient's cornea upon removal of a corneal plug from an area of the patient's cornea remaining after a partial, thickness of outer layers of corneal tissue has been removed from the cornea and a replacement cap component sized and shaped to simulate the dimensions and curvature of the outermost surface of a cornea and of a sufficient thickness to replace a thickness of outer layers which includes epithelium, Bowman's membrane and corneal stroma. The replacement plug component and the replacement cap component may both be made of an optically clear artificial material or one of the components may be made of an optically clear artificial material while the other component is made of a biologically derived material. In one embodiment, the prosthesis also includes a tissue carrier bonded thereto, the carrier comprising preserved tissue adapted for attachment to an eye.

In a preferred embodiment, the prosthesis is attached to the tissue carrier by an adhesive bond, the adhesive preferably being comprised of an adhesive polyphenolic protein, such as the type derived from the mussel genus Mytilus. The use of polyphenolic protein provides great advantages over many other adhesives which are prone to hydrate and/or adhesively fail when continuously exposed to water. Indeed, the mussel from which the protein is derived uses such polyphenolic proteins to permanently adhere to a variety of surfaces under sea water, with adhesion strengths in excess of about $10^2 lb/in^2$ (about $10^6 N/m^2$). In yet another embodiment the tissue carrier is merely the polyphenolic protein itself, polymerized as the prosthesis is attached to the cornea.

BEST MODE FOR CARRYING OUT THE INVENTION

Figure 1:
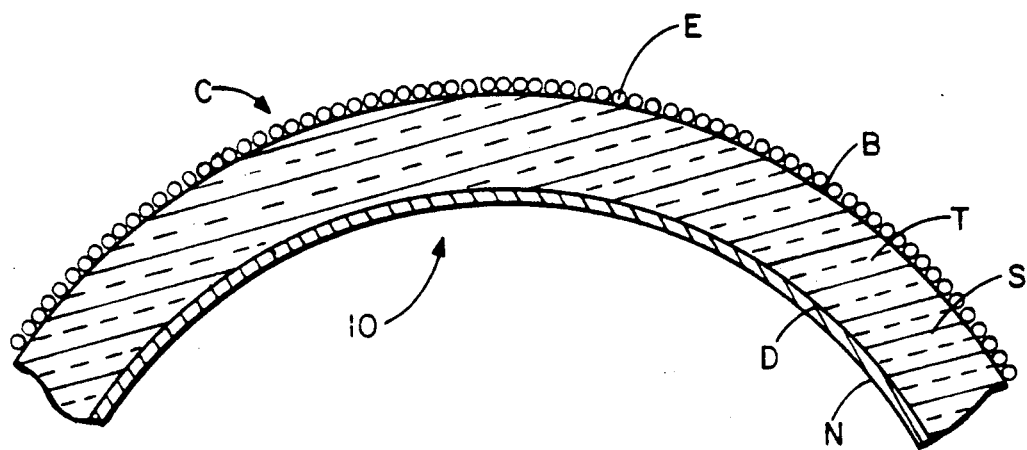
FIG. 1 is a partial cross-sectional view of the corneal-scleral rim of a human eye.

FIG. 1 is a partial cross-sectional view of the corneal-scleral rim of a human eye wherein the layers of the cornea C are shown diagrammatically. The outermost layer of the cornea, the epithelial layer, is shown as E. Moving inwardly in the cornea is the Bowman's membrane, shown as B. Immediately adjacent the Bowman's membrane is the stroma of the cornea, shown as T. The Descemet's membrane adjacent the stroma is shown as D, and the corneal endothelium is shown as N. The sclera is designated as S in the figure.

Figure 2:
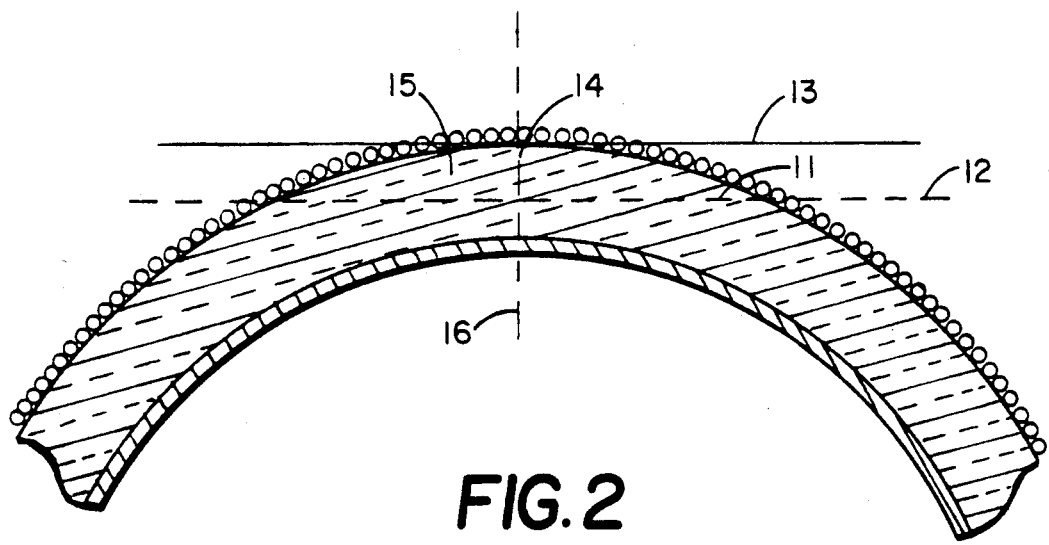
FIG. 2 is a partial cross-sectional view of the corneal-scleral rim of a human eye.
Figure 3:
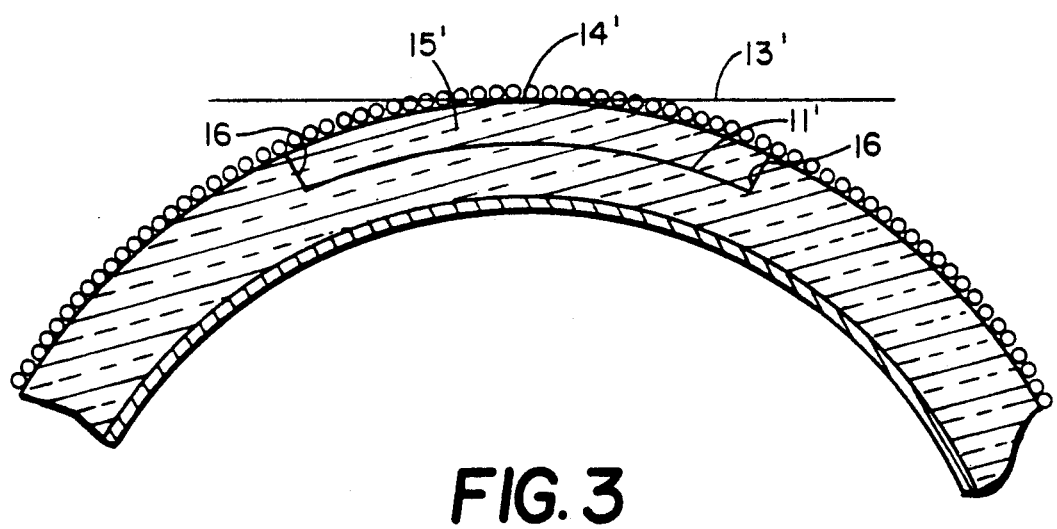
FIG. 3 is a partial cross-sectional view of the corneal-scleral rim of a human eye.

A donor replacement cap of corneal tissue from the cornea of a donor eye may be prepared using well known preparation techniques. Briefly, a donor globe must be cleaned and the outer layers of epithelial cells and stroma removed to a variable depth using a generally transverse cut. As shown in FIG. 2, the transverse cut 11 will desirably be made along an axis 12 that is generally parallel to a tangent 13 of the center 14 of the outermost surface of the thickness 15 of the cornea that is being removed. In a preferred embodiment, the tangent 13 will be generally perpendicular to the axis of vision 16. The transverse cut may be made flat as shown in FIG. 2 or it may be curved as shown in FIG. 3. To obtain a curved cut the surgeon may cut into the eye a predetermined distance (cuts into cornea represented as 16) and then make a generally transverse cut 11 which is curved while still being generally parallel to the tangent 13' of the center 14' of the outermost surface of the thickness 15' of the cornea being removed.

Figure 4:
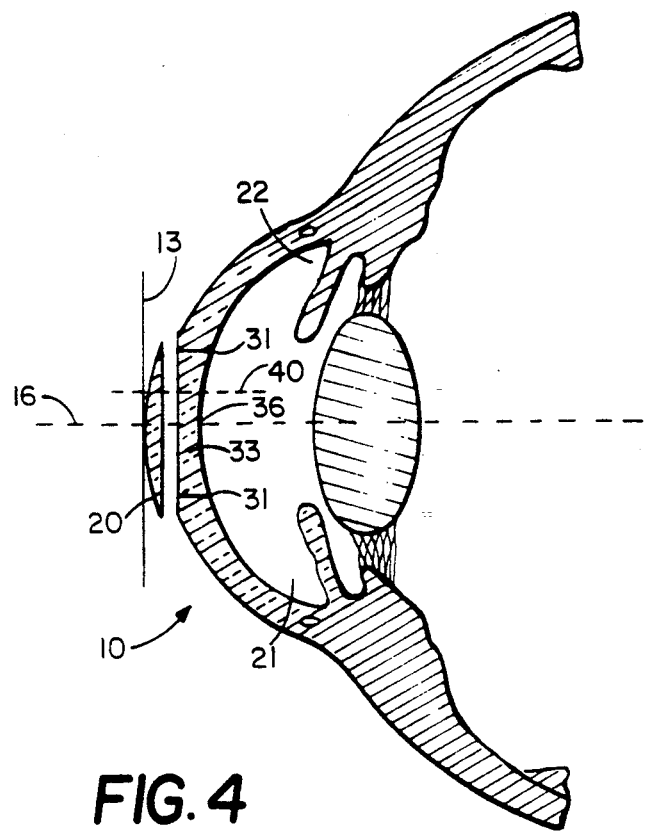
FIG. 4 is a cross-sectional view of the anterior portion of a human eye showing an excised portion of tissue.

Once the outer layers of corneal tissue have been removed, a corneal-scleral rim 10 is excised from the donor cornea, as shown in FIG. 4. (Line 21 represents the cuts made into the eye to excise the rim.) FIG. 4 shows a cross-sectional view of the front portion of a donor eye from which a cap 20 comprising a thickness of outer layers of tissue has been removed by a surgeon using a generally transverse cut. The excised portion of the cornea is placed in an appropriate preserving medium, such as gluteraldehyde or formalin, where it may be stored for a period of days, weeks, or even months. The donor cap removed from the donor eye with the transverse cut may also be preserved and used in a partial thickness transplant or as a donor cap in the transplantation method of this invention.

Figure 5:
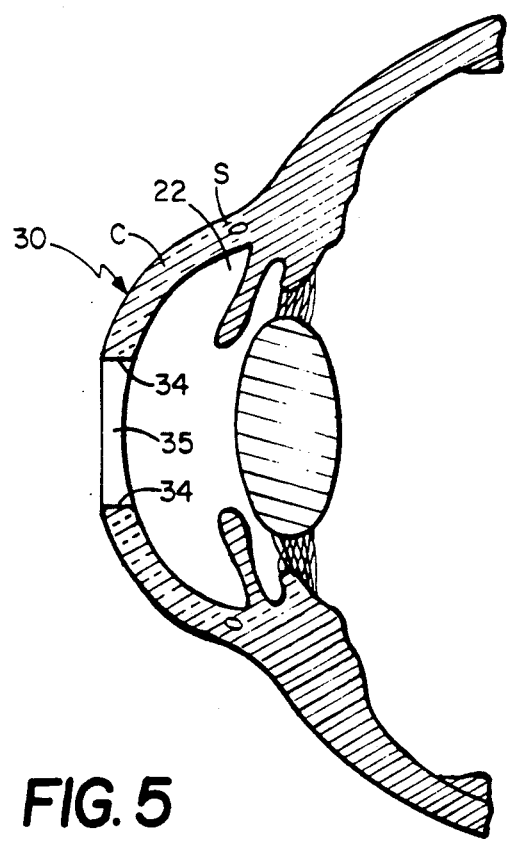
FIG. 5 is a cross-sectional view of the anterior portion of a human eye showing an excised portion of tissue.

During a corneal endothelium transplant of this invention, the patient-recipient cornea will be prepared by first removing a partial thickness of outer layers of corneal tissue. In the portion of the patient recipient's cornea remaining after the thickness has been removed, shown as 30 in FIG. 5, the surgeon cuts into the cornea (cuts represented as 31) and removes a plug 33 of diseased or damaged cornea comprising Descemet's membrane D and corneal endothelium N, the remaining corneal tissue rim 34 forming a bore 35 through the cornea.

Figure 6:
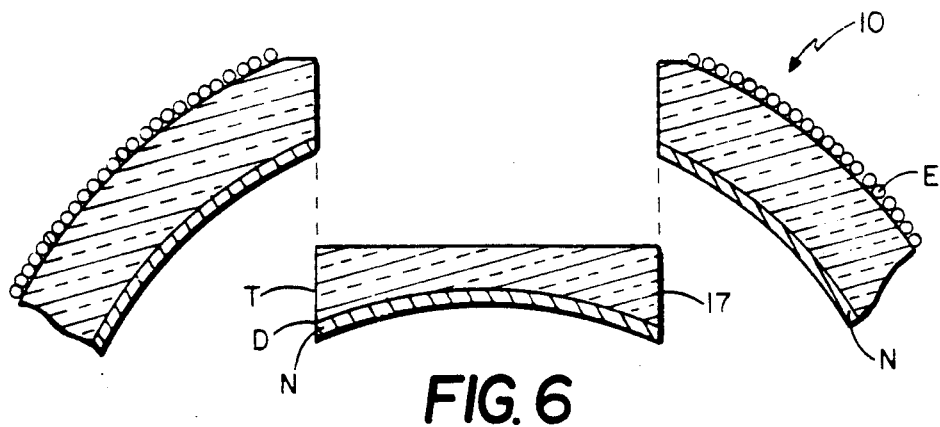
FIG. 6 is a partial cross-sectional view of the corneal-scleral rim of a human eye showing an excised portion of tissue.

Upon completion of the removal of the patient's corneal plug 33, the corneal-scleral rim of the donor cornea, 10 in FIG. 6, is cut with the endothelial surface N up to form a donor replacement plug 17 comprising the posterior layers of the donor's cornea, the donor plug 17 having substantially the same dimensions as the corneal plug 33 being replaced.

As shown in FIG. 4 the cuts 31 made into the cornea o remove a plug of donor or patient corneal tissue will desirably be made along an axis 40 that is generally perpendicular to the tangent line 13 through the center of the outermost surface of the cornea, the tangent being substantially perpendicular to the line of vision 16. In a preferred embodiment, the plug of corneal patient tissue 33 will be removed from the center 36 of the area of cornea remaining after the thickness of outer layers of tissue was removed. The donor and patient corneal plugs are desirably generally cylindrical.

The transverse dimensions of the thickness of outer layers of tissue removed from the patient's or donor's cornea will desirably be equal to or greater than the transverse dimensions of the donor or patient corneal plug. It is to be understood that the transverse dimensions of the thickness and plug will differ but preferably the transverse dimensions of the plug will be only slightly less than the transverse dimensions of the thickness, so that the plug's transverse dimensions will be in the range of 80%-90% of the transverse dimensions of the outer thickness.

After the patient plug has been removed, the donor replacement plug may then be transferred and inserted into position in the recipient patient's cornea and secured in place by well known techniques, preferably with direct sutures. Once the posterior layers of the cornea have been replaced, then a replacement cap that is the partial thickness of outer layers of corneal tissue removed from the patient s cornea or a donor cap that is a similar thickness of outer layers of corneal tissue from a donor eye will be placed over the area of the patient's cornea from which the thickness of tissue was removed and over the replacement plug and secured in place with known attachment means, preferably with direct sutures.

Figure 7:
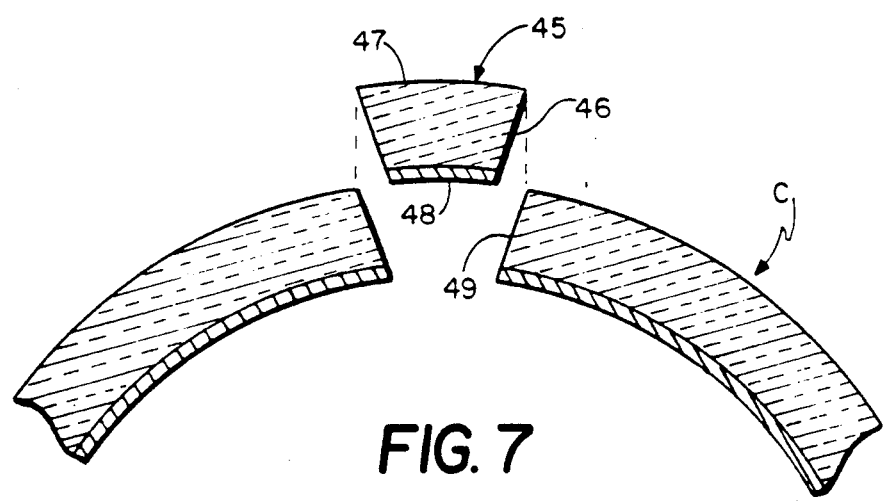
FIG. 7 is a partial cross-sectional view of the corneal-scleral rim of a human eye.

Referring to FIG. 7, another method of the invention is shown which comprises the steps of cutting through the full thickness of a patient's cornea C to form a plug 45 having a beveled edge 46 and an inner and outer surface 47, 48 and wherein the beveled edge slopes inwardly toward the center of the cornea from the outer surface to the inner surface, removing the plug from the cornea thereby forming a bore 49 through the remaining portion of the patient's cornea, and placing into the bore an ocular implant (not shown) sized and shaped to fit closely in the bore.

Any suitable instrument can be employed in making the cuts into the cornea, such as, a trephine of the type normally used in full thickness transplant procedures, a knife, motorized slicer, or laser. Similarly, any suitable instruments can be employed in making a transverse cut, such as a knife, motorized slicer, or laser.

The ocular implant used with a method of the invention may comprise fresh or preserved tissue or artificial tissue material either synthesized or derived from a biological source.

Figure 8:
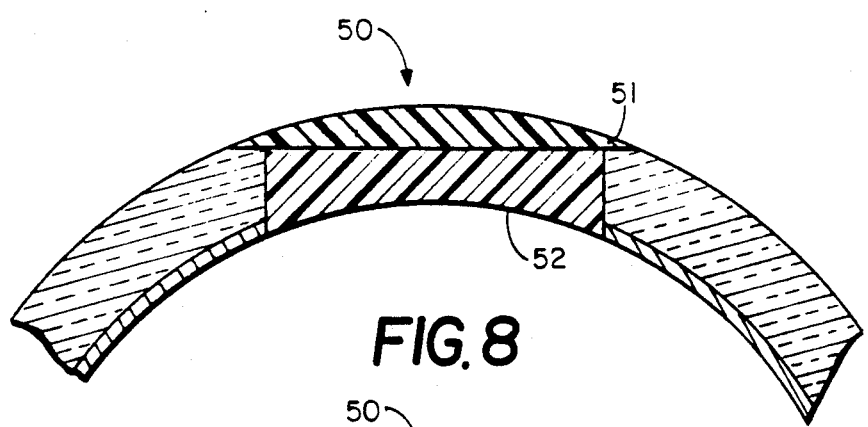
FIG. 8 is a cross-sectional view of a cornea showing a modified embodiment of the prosthesis of the invention implanted.
Figure 9:
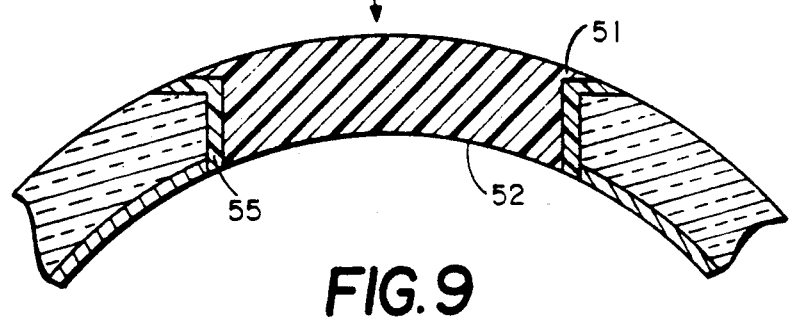
FIG. 9 is a cross-sectional view of a cornea showing a modified embodiment of the prosthesis of the invention implanted.

The invention also relates to an ocular prosthesis shown in FIG. 8 implanted in a cornea. The ocular prosthesis 50 comprises a replacement cap component 51 having a slightly domed anterior surface, the component being sized and configured to replace a partial thickness anterior portion of a cornea of an eye, the thickness being replaced including epithelial layer, Bowman's membrane and corneal stroma and a replacement plug component 52 extending posteriorly from the posterior surface of the anterior portion, sized and configured to replace a full thickness portion of the cornea, the plug component having a width or diameter smaller than the width or diameter of the cap component. The prosthesis may be formed as an integral unit or the two components may be attached to each other using any known attachment means such as adhesives and the like.

The prosthesis will desirably be of a material that can be sized and configured to fit the dimensions of the corneal tissue to be removed from a patient's cornea either before surgery or by the surgeon after the patient's tissue has been removed. Artificial materials which may be used in manufacturing a prosthesis of this invention or components thereof include but are not limited to biologically derived and processed materials and synthesized materials.

"Biologically derived and processed" as those terms are used in this description means that the material has been taken from a biological source and processed in such a way that its macroscopic structure has been altered from its naturally occurring state. An example of a biologically derived and processed material is collagen which has been isolated and purified from porcine tissue. The isolated collagen may be identical on a molecular level to naturally occurring collegen but its macroscopic structure is altered by the isolation process so that the collagen no longer has a fibrous structure as is found in naturally occurring collagen. Synthesized materials may include synthetic polymers such as polymethyl methacrylate. polycabonates, HEMA, polysulfones, silicones and synthetic materials fabricated to resemble naturally occurring substances.

The ocular prosthesis of this invention may further include a carrier 55 attached thereto, the carrier comprising preserved denatured tissue adapted for attachment to an eye. The carrier is desirably constructed of preserved biological tissue. The tissue may be of any suitable material, including cornea, sclera, fascia or other connective tissues such as tendon, cartilage or bone. Corneal tissue is preferred for those embodiments which require the carrier 55 to be transparent. The tissue must be preserved in a fashion which generally maintains the structural integrity of the extra-cellular collagen architectural matrix. Such preservation processes include but are not necessarily limited to glycerin dehydration, alcohol preservation, gluteraldehyde preservation, and formalin preservation. Preferably the preservation process denatures the tissue, analogously to tanning of rawhide, resulting in a number of benefits as described below.

In a preferred method of preserving such tissue, biological tissue, such as sclera, is removed, cleaned, and placed into preservative such as gluteraldehyde or formalin, where it may be stored for a period of days, weeks, or even months. When desired, the tissue is removed from the preservative and, if not already in proper configuration, manufactured into the appropriate configuration. The tissue is then united with the ocular prosthesis as described herein, and the resulting prosthesis is placed in a preservative that is compatible with the prosthesis material such as formalin. It should be noted that some prosthesis materials, such as PMMA, are incompatible with alcohol, but are compatible with other preservatives such as formalin, which is therefore a particularly preferred preservative for storage of the manufactured prosthesis. Desirably the preservative denatures the tissue. Denaturing may alter the antigenicity of the tissue to reduce or eliminate rejection complications, and in certain circumstances may permit use of biological tissue from other species. Denaturing also may tend to inhibit vascularization, a particularly desirable effect if the tissue is cornea. In most instances, the tissue is stored at least about three days in the preservative before use.

Manufacture of tissue into the appropriate physical configurations can be accomplished by well known techniques including the use of microkeratomes and trephines. See, e.g., Kaufman, "The Correction of Aphakia," 89 *American Journal of Ophthalmology*. 1 (Jan. 1980); Leigh, "Treatment of Gross Corneal Opacification by Lamellar and Annular Lamellar Keratoplasty," 39 *Brit. J. Ophthal.* 641 (1955); Waring, *Refractive Keratoplasty*. 31 Resident & Staff Physician, 25–34 (May, 1985).

The prosthesis 50 may be attached to the preserved tissue carrier 55 by any suitable means, including but not limited to any of a variety of biologically acceptable adhesives. Such adhesives must be characterized by their ability to form a liquid-tight bond between the material of the prosthesis 50 and the preserved tissue carrier 55. Among adhesives suitable for this purpose are various well known dental adhesives. In particular, applicant has used an adhesive sold by Johnson & Johnson under the product number 2748. This two-part adhesive has successfully bonded both formalin and gluteraldehyde preserved tissue to a polymethyl methacrylate prosthesis.

A particularly preferred class of adhesives are the bioadhesive polyphenolic proteins, such as that derived from the mussel genus Mytilus. These adhesives are characterized by a very low aqueous dispersive effect probably due, at least in part, to the high amounts of hydroxyproline (Hyp) and 3,4-dihyroxyphenylalanine (Dopa) present in the proteins. These adhesives have very low solubility at neutral or slightly basic pH, and adhere to many substrates, including biological substrates, durably in the presence of water, apparently for many years. They are particularly preferred for their long term durability under wet/humid conditions, for their ability to be applied to a wet substrate and for their ability to bond durably to collagenous substrates. Furthermore, as they are biologically derived adhesives, they are likely to be biologically compatible in most forms.

These bioadhesive proteins may be isolated from the phenol glands of mussels according to well known techniques, including those described in Waite and Tanzer, *Science*. 212, 1038 (May 21, 1981); and U.S. Pat. No. 4,496,397, "Process for Purifying and Stabilizing Catechol-Containing Proteins and Materials Obtained Thereby," J. Waite (Jan. 29, 1985).

Such polyphenolic proteins appear to be characterized by including repeating decapeptide units having the following chemical formula:

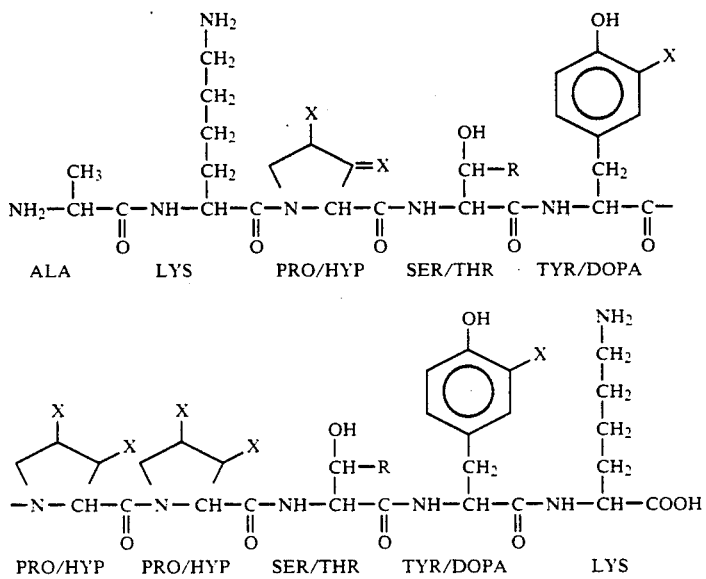

where each X is either hydroxyl or hydrogen, and each R is either hydrogen or methyl.

Such decapeptides may be prepared and isolated according to the methods reported in U.S. Pat. No. 4,687,740, "Decapeptides Produced From Bioadhesive Polyphenolic Proteins," J. Waite (Aug. 18, 1987). Furthermore, such decapeptides may be polymerized to form large polyphenolic molecules having up to 1000 such repeating units, the linking group being an amino acid, an oligopeptide or a bifunctional spacer, as set forth in U.S. Pat. No. 4,687,740. European Pat. Application No. 87105775, published Nov. 11, 1987 (EP 244688) reports preferred adhesive formulations prepared utilizing such polyphenolic proteins. The formulations include the decapeptide unit, either singly or in polymerized form, together with a crosslinking agent (such as mushroom tyrosinase) and additional optional additives such as surfactants (such as SDS) and filler (such as collagen). Other methods for manufacturing such polyphenolic proteins are described in European Pat. Application No. 87104853 (published as EP 242656, Oct. 28, 1987), and A. C. Jouanneau, "A New Bio-Adhesive: A Protein Extract of Mussels--Attempts to Produce This Adhesive from Mytilus Edulis by Genetic Engineering," Biofutur (41, 65–66) 1985 (French). From the foregoing, it is seen that such bioadhesive polyphenolic proteins may be obtained through isolating them from natural producers of the proteins (i.e., the mussels themselves), or by synthesizing or genetically engineering them through standard techniques. Furthermore, as the unique adhesive properties of these proteins are believed to result from the presence of Dopa and hydroxyproline, certain changes in the remaining molecular structure of the proteins, likely including some amino acid substitutions (probably other than the Dopa and Hyp units), are likely to be possible to control and/or select properties of the bioadhesive.

In the corneal endothelial tissue replacement procedure using a prosthesis of this invention, the eye is immobilized and the corneal portion to be removed is excised as described above employing suitable instruments. Upon completion of the removal of the corneal tissue, the prosthesis of the invention is inserted into the bore defined by the rim of the cornea. During the procedure, the prosthesis is supported by a suitable handle or grip such as a small suction cup applied to the outer, domed surface of the prosthesis 54. Desirably, small sutures are taken about the periphery of the carrier 55 and are passed through the cornea to anchor the carrier 55 in place. Alternatively or in addition, a suitable adhesive such as a bioadhesive polyphenolic protein may be applied to the mating surfaces to securely bond them. The generally tight fit between the carrier and the corneal tissue rim assures that no leakage of aqueous humor from the eye will occur. Post operative procedures are similar to those commonly employed in corneal transplant surgery.

The carrier 55 is easily sutured or adhesively bonded (as by utilizing the polyphenolic protein adhesives described above) to the cornea (C), as the carrier is quite durable. The interstices within the carrier's collagen matrix, which are not substantially affected by the preferred denaturization, permit host-tissue cells to migrate and grow therein, laying down new collagen which interdigitates to form a "living bond" between the carrier 55 and the cornea (C). The carrier 55 may be of any suitable radial thickness, desirably at least 1 mm to provide sufficient tissue for suturing, and preferably between about 1.5 mm and about 3 mm. As described below, however, the carrier 55 may be substantially larger.

Further, the invention relates to a method of surgically repairing the cornea of an eye, comprising the steps of removing at least a partial thickness of the eye wall, including corneal tissue; and attaching an ocular prosthesis having a transparent prosthesis of biologically acceptable material to the eye wall covering the area from which tissue was removed. The attachment step is accomplished by applying to the prosthesis or the cornea, or both, polymerizable adhesive polyphenolic protein such as the type derived from the mussel genus Mytilus, and then polymerizing the protein to form a permanent adhesive bond therebetween.

The use of the methods of corneal transplantation of this invention provide significant advantages over the corneal transplant procedures of the prior art.

When a partial full thickness transplant is performed using known transplantation techniques a cylindrical plug of all layers of cornea is typically removed from a patient's cornea by cutting into the corner from the outer surface to the posterior endothelial surface using a trephine. The surgeon then uses the same trephine to remove a cylindrical plug of donor tissue that is similar in size and shape to the removed plug from a corneal-scleral rim excised from a healthy donor eye.

The endothelial cell layer of the cornea is very fragile and should not be touched during the transplantation procedure. In order to obtain a cylindrical plug of donor tissue from an excised corneal-scleral rim the surgeon must lay the rim on a cutting surface with the epithelial cell side contacting the cutting surface and cut into the tissue from the endothelial side. The cutting process results in the walls of the plug and the walls of the remaining tissue which form a bore through the cornea remaining in the rim being slightly deformed by the cutting edge of the instrument. Because the plug removed from the patient's cornea is cut from the epithelial cell side in and the plug replacing the patient's tissue is cut from the endothelial side out, when the donor plug is placed in the patient's cornea the fit is not exact which is likely to result in the outer surface of the plug extending past the outer surface of the patient's cornea or falling short of the outer surface of the patient's cornea causing the outer surface of the cornea to be slightly deformed and resulting in regular and irregular astigmatism.

The transplantation method of this invention greatly reduces the occurrence of such regular and irregular astigmatism because the outer layers of the corneal surface of both the patient and donor eye are removed using a transverse cut so the deformation caused by the cutting surface will be similar in both the posterior surface of the thickness of outer layers and the anterior surface of the cornea remaining after a thickness of outer layers has been removed.

A second advantage the methods of this invention provides over the use of a partial full thickness transplant of the prior art is that if the outer layers of the patient's cornea are healthy they can be reattached to the patient's cornea after the diseased or injured deep layers have been replaced. When the patient's own tissue is reattached, change in the curvature of the outermost surface of the cornea occurring as a result of the procedure will be minimal and the amount of transplanted foreign tissue (i.e., from donor eye) will be less than with a standard penetrating transplant (i.e., less tissue for a given diameter) which will decrease the likelihood of rejection and failure of the transplant. Moreover, since the blood vessels of the cornea are generally found in the outer layers, the foreign tissue placed in the deeper layers of the cornea will be separated from the blood vessels. This is an important advantage because the cells of the patient's immune system which cause rejection of foreign tissue are carried through the patient's body in the blood.

Another advantage of the method of this invention is that because a thickness of outer layers of the cornea is removed from the patient's cornea, the front or back refractive surface of that thickness of the cornea can be altered to change the refractive state of the eye. This may be done by either the donor tissue processer or the surgical team.

It should be understood that the steps of the methods of this invention described herein may be separated over time and accomplished in stages, even including two or more surgical procedures.

While a preferred embodiment of the present invention has been described, it should be understood that various changes, adaptations and modifications may be made therein without departing from the spirit of the invention and the scope of the appended claims.

What is claimed is:

1. A method of corneal transplantation comprising the steps of:
   (a) removing a partial outer thickness of tissue from a patient's cornea by making a cut generally transverse to the axis of vision;
   (b) removing a plug of the patient's source from the area in which the outer thickness of tissue was removed, the plug including Descemet's membrane and corneal endothelial cells, thereby forming a bore through the patient's cornea;

(c) placing in said bore a donor replacement plug including Descemet's membrane and corneal endothelium cut from the cornea of a donor eye, the plug being sized and shaped to fit closely in said bore;

(d) surgically attaching said replacement plug to the patient's cornea; and (e) surgically reattaching to the patient's cornea the thickness of corneal tissue previously removed from the patient's cornea.

2. A method of corneal transplantation comprising the steps of:

(a) removing a partial outer thickness of tissue from a patient's cornea by making a cut generally transverse to the axis of vision;

(b) removing a plug of the patient's cornea from the area in which the outer thickness of tissue was removed, the plug including Descemet's membrane and corneal endothelial cells, thereby forming a bore through the patient's cornea;

(c) placing in said bore a donor replacement plug including Descemet's membrane and corneal endothelium cut from the cornea of a donor eye, the plug being sized and shaped to fit closely in said bore;

(d) attaching the donor plug to the patient's cornea; and (e) attaching to the patient's cornea or corneal replacement cap comprising a generally circular outer thickness of corneal tissue taken from a cornea of a donor eye using a generally transverse cut to cover the area from which the outer thickness of the patient's cornea was removed.

3. The method of claim 2, further comprising the step of removing from a cornea of a donor eye a partial outer thickness of corneal tissue using a generally transverse cut.

4. The method of claim 3, further comprising the step of removing from the portion of the donor cornea remaining after the outer thickness has been removed a corneal-scleral rim that includes Descemet's membrane and corneal endothelial cells.

5. The method of claim 4, further comprising the step of forming a bore through the corneal-scleral rim in the area in which the outer thickness of tissue was removed to define a donor plug that includes Descemet's membrane and corneal endothilial cells.

6. A method of corneal transplantation comprising the steps of:

(a) removing a partial, generally circular outer thickness of tissue from a donor cornea by making a cut generally transverse to the axis of vision;

(b) excising from the donor cornea a corneal-scleral rim that includes Descemet's membrane and corneal endothelium of the donor cornea and the portion of the donor cornea from which the outer thickness was removed.

(c) removing a partial, generally circular outer thickness of tissue from a patient s cornea by making a cut generally transverse to the axis of vision;

(d) removing a plug of the patient's cornea from the area in which the outer thickness of tissue was removed, the plug including Descemet's membrane and corneal endothelial cells, thereby forming a bore through the remaining portion of the patient's cornea; and (e) removing a donor plug of the remaining portion of the corneal-scleral rim from the area in which the outer thickness of tissue was removed, the donor plug including Descemet's membrane and corneal endothelial cells;

(f) placing in said bore the donor plug; and (g) reattaching the outer thickness of tissue removed from the patient's cornea to the patient's cornea to cover the plug and to cover the area of the patient's cornea from which the outer thickness of tissue was removed.

7. A method of corneal transplantation comprising the steps of:

(a) removing a partial, generally circular outer thickness of tissue from a patient's cornea by making a cut generally transverse to the axis of vision;

(b) removing a plug of the remaining portion of the patient's cornea from the area in which the outer thickness of tissue was removed, the plug including Descemet's membrane and corneal endothelial cells, thereby forming a bore through the remaining portion of the patient's cornea; and (c) placing in said bore a donor plug that includes Descemet's membrane and corneal endothelium from the cornea of a donor eye;

(d) surgically attaching the plug to the cornea; and (e) reattaching to the cornea the generally circular outer thickness of corneal tissue removed from the patient's cornea to cover the area from which the outer thickness of tissue was previously removed.

8. A method of corneal transplantation comprising the steps of:

(a) removing a partial, generally circular outer thickness of tissue from a patient's cornea by making a cut generally transverse to the axis of vision;

(b) removing a plug of the remaining portion of the patient's cornea from the area in which the outer thickness of tissue was removed, the plug including Descemet's membrane and corneal endothelial cells, thereby forming a bore through the remaining portion of the patient's cornea; and (c) placing in said bore a donor plug that includes Descemet's membrane and corneal endothelium from the cornea of a donor eye;

(d) attaching the plug to the cornea; and (e) attaching to the cornea a generally circular outer thickness of corneal tissue from a cornea of a donor eye to cover the area from which the outer thickness of tissue was previously removed.

9. A method of corneal transplantation comprising the steps of:

(a) removing a partial, generally circular outer thickness of tissue from a donor cornea by making a cut substantially perpendicular to the axis of vision;

(b) excising from the donor cornea a corneal-scleral rim that includes Descemet's membrane and corneal endothelium of the donor cornea and the portion of the donor cornea from which the outer thickness was removed.

(c) removing a partial, generally circular outer thickness of tissue from a patient's cornea by making a cut substantially perpendicular to the axis of vision;

(d) removing a plug of the patient's cornea from the area in which the outer thickness of tissue was removed, the plug including Descemet's membrane and corneal endothelial cells, thereby forming a bore through the remaining portion of the patient's cornea; and (e) removing a donor plug of the corneal-scleral rim from the area in which the outer thickness of tissue was removed, the donor plug including Descement's membrane and corneal endothelial cells;

(f) placing in said bore the donor plug; and (g) attaching to the patient's cornea the outer thickness of tissue removed from a donor cornea to cover the plug and to cover the area of the patient's cornea from which the outer thickness of tissue was removed.

10. A method of replacing damaged or diseased corneal endothelium comprising the steps of:

(a) removing a thickness of corneal tissue including corneal endothelium from a patient's cornea thereby forming a bore through the remaining corneal tissue, the thickness having a beveled edge and an inner and outer surface and wherein the beveled edge slopes toward the center of the cornea from the outer surface to the inner surface; and (b) placing i said bore an ocular implant sized and shaped to fit closely in said bore.

11. A method of corneal transplantation comprising the steps of:

(a) removing a partial outer thickness of tissue from a patient's cornea to define a first cap by making a cut substantially perpendicular to the axis of vision;

(b) forming a bore through the remaining portion of the patient's cornea in the area from which the first cap was removed;

(c) removing a partial outer thickness of tissue from a donor's cornea to define a second cap by making a cut substantially perpendicular to the axis of vision;

(d) forming a bore through the remaining portion of the donor's cornea in the area from which the second cap was removed to define a plug including Descemet's membrane and corneal endothelium;

(e) affixing the plug in the bore through the patient's cornea; and (f) affixing one of the first or second caps to the patient's cornea to cover the area thereof from which the first cap was removed.

12. The method of claim 11 wherein the first and second caps are substantially equal in transverse dimension, the plug being formed to have a transverse dimension of between about 80 and about 90 percent of the transverse dimension of either the first or second cap.

* * * * *